(12) United States Patent
Lachner

(10) Patent No.: US 8,394,448 B2
(45) Date of Patent: Mar. 12, 2013

(54) FLEXIBLE AND PLASTIC RADIOPAQUE LAMINATE COMPOSITION

(75) Inventor: Thomas F. Lachner, Lake Bluff, IL (US)

(73) Assignee: Merit Medical Systems, Inc., South Jordan, UT (US)

(*) Notice: Subject to any disclaimer, the term of this patent is extended or adjusted under 35 U.S.C. 154(b) by 56 days.

(21) Appl. No.: 12/549,241

(22) Filed: Aug. 27, 2009

(65) Prior Publication Data

US 2009/0318895 A1    Dec. 24, 2009

Related U.S. Application Data

(62) Division of application No. 11/083,842, filed on Mar. 18, 2005, now abandoned.

(51) Int. Cl.
| | |
|---|---|
| B29D 22/02 | (2006.01) |
| B29D 23/00 | (2006.01) |
| B32B 1/08 | (2006.01) |
| B32B 15/08 | (2006.01) |
| A61M 29/00 | (2006.01) |
| A61M 36/00 | (2006.01) |
| B05D 7/00 | (2006.01) |

(52) U.S. Cl. ............ 427/2.25; 427/2.3; 427/5; 427/180; 428/34.1; 428/35.7; 428/36.91; 428/36.92; 428/615; 606/194; 606/108

(58) Field of Classification Search .......... 427/2.1–2.31, 427/306, 299, 2.25, 2.3, 180, 212, 222, 427; 428/35.7, 34.1, 36.92, 615, 425.9
See application file for complete search history.

(56) References Cited

U.S. PATENT DOCUMENTS

| | | | |
|---|---|---|---|
| 3,181,926 A | * | 5/1965 | Busche .............................. 8/510 |
| 3,314,430 A | | 4/1967 | Alley et al. |
| 3,788,328 A | | 1/1974 | Alley et al. |
| 4,199,623 A | * | 4/1980 | Nuzzi et al. ..................... 427/305 |
| 4,516,970 A | | 5/1985 | Kaufman et al. |
| 4,681,110 A | | 7/1987 | Wiktor |
| 5,045,071 A | | 9/1991 | McCormick et al. |
| 5,084,022 A | | 1/1992 | Claude |
| 5,114,401 A | | 5/1992 | Stuart et al. |
| 5,116,652 A | | 5/1992 | Alzner |
| 5,203,777 A | | 4/1993 | Lee |
| 5,217,440 A | * | 6/1993 | Frassica ......................... 604/524 |

(Continued)

FOREIGN PATENT DOCUMENTS

| | | |
|---|---|---|
| DE | 19635951 C1 | * 11/1997 |
| EP | 987042 | 3/2000 |

OTHER PUBLICATIONS

Notification of Transmittal of the International Search Report and the Written Opinion of the International Searching Authority issued Jun. 8, 2009 in International Application No. PCT/US2009/040355.
Restriction Requirement issued Jun. 1, 2007 in co-pending U.S. Appl. No. 11/083,842.

(Continued)

*Primary Examiner* — Timothy Meeks
*Assistant Examiner* — Cachet Sellman
(74) *Attorney, Agent, or Firm* — Stoel Rives LLP

(57) ABSTRACT

A flexible laminate composition and methods for manufacturing same are provided. The flexible laminate composition includes one or more discrete and separate layers of a radiopaque material wherein the radiopaque layer is applied via a solvent to a layer that is composed of a plastic material. The laminate composition can be formed into a radiopaque marker band that can be used with a medical device, such as a catheter, for radiographic imaging. The laminate composition as an alternative can also be utilized to form the catheter or other suitable medical device.

8 Claims, 1 Drawing Sheet

U.S. PATENT DOCUMENTS

| | | | |
|---|---|---|---|
| 5,253,653 A | 10/1993 | Daigle et al. | |
| 5,267,574 A | 12/1993 | Viera et al. | |
| 5,300,048 A | 4/1994 | Drewes, Jr. et al. | |
| 5,416,822 A * | 5/1995 | Kunik | 378/162 |
| 5,558,652 A | 9/1996 | Henke | |
| 5,820,918 A * | 10/1998 | Ronan et al. | 427/2.1 |
| 5,858,556 A * | 1/1999 | Eckert et al. | 428/586 |
| 5,948,489 A | 9/1999 | Hopkins | |
| 6,036,682 A | 3/2000 | Lange et al. | |
| 6,261,260 B1 * | 7/2001 | Maki et al. | 604/103.07 |
| 6,277,108 B1 | 8/2001 | McBroom et al. | |
| 6,375,660 B1 * | 4/2002 | Fischell et al. | 606/108 |
| 6,540,721 B1 * | 4/2003 | Voyles et al. | 604/103.1 |
| 6,623,823 B1 * | 9/2003 | Onwumere | 428/36.91 |
| 6,635,082 B1 * | 10/2003 | Hossainy et al. | 623/1.15 |
| 6,638,245 B2 | 10/2003 | Miller et al. | |
| 7,077,837 B2 * | 7/2006 | Sahagian | 623/1.15 |
| 2002/0198559 A1 * | 12/2002 | Mistry et al. | 606/194 |
| 2003/0023190 A1 * | 1/2003 | Cox | 600/585 |
| 2003/0167052 A1 | 9/2003 | Lee et al. | |
| 2005/0004649 A1 * | 1/2005 | Mistry et al. | 623/1.11 |
| 2005/0064223 A1 * | 3/2005 | Bavaro et al. | 428/615 |
| 2005/0065434 A1 | 3/2005 | Barao et al. | |
| 2005/0283226 A1 * | 12/2005 | Haverkost | 623/1.15 |
| 2006/0201601 A1 | 9/2006 | Furst et al. | |
| 2006/0210700 A1 | 9/2006 | Lachner | |
| 2008/0097394 A1 | 4/2008 | Lampropoulos et al. | |
| 2009/0326560 A1 | 12/2009 | Lampropoulos et al. | |

OTHER PUBLICATIONS

Response to Restriction Requirement filed Aug. 30, 2007 in co-pending U.S. Appl. No. 11/083,842.
Office Action issued Nov. 19, 2007 in co-pending U.S. Appl. No. 11/083,842.
Amendment and Response filed May 19, 2008 in co-pending U.S. Appl. No. 11/083,842.
Office Action issued Sep. 17, 2008 in co-pending U.S. Appl. No. 11/083,842.
Interview Summary issued Dec. 15, 2008 in co-pending U.S. Appl. No. 11/083,842.
Amendment and Response filed Mar. 17, 2009 in co-pending U.S. Appl. No. 11/083,842.
Notice of Non-Compliant Amendment issued Jul. 2, 2009 in co-pending U.S. Appl. No. 11/083,842.
Notice of Abandonment issued Jan. 27, 2010 in co-pending U.S. Appl. No. 11/083,842.
Preliminary Amendment filed May 15, 2009 in co-pending U.S. Appl. No. 12/147,933.
Office Action dated May 24, 2011 in U.S. Appl. No. 12/147,933.
Office Action dated Jan. 13, 2012 for U.S. Appl. No. 12/147,933.
European Search Report dated Aug. 19, 2011 for EP09770595.8 (PCT/US2009/040355).
Office Action dated Aug. 13, 2012 for U.S. Appl. No. 12/147,933.

* cited by examiner

FLEXIBLE AND PLASTIC RADIOPAQUE LAMINATE COMPOSITION

CROSS REFERENCE TO RELATED APPLICATIONS

This application is a divisional application of U.S. patent application Ser. No. 11/083,842, now abandoned, entitled "A Flexible and Plastic Radiopaque Laminate Composition," filed on Mar. 18, 2005, the entire specification of which is incorporated herein by reference.

BACKGROUND OF THE INVENTION

The present invention relates to laminate compositions. More specifically, the present invention relates to flexible and plastic laminate compositions that include a discrete and separate layer of a radiopaque material.

The use and manufacture of radiopaque materials compounded into plastic resins and then extruded into tubing or molded into shapes is well known. Radiopaque qualities are imparted to plastics through the dispersion of radiopaque materials into the thermoplastic resin. The resin is then extruded into tubes or molded into shapes that are desirable for use. In order for these resins to be radiopaque, the resins must be loaded with high percentages of radiopaque materials. This high percentage of loading can create structural and functional problems with the materials.

The use of a thin metal layer that can impart radiopaque qualities is also known. For example, ion implantation and vapor deposition processes can be utilized to deposit a thin layer of metal on the surface of medical devices. Electrodeposition processing techniques are also known that can apply a metal layer to the surface of medical devices. These types of processes are effective at producing a thin layer of radiopaque metal on the surface of the plastic. As a result, a high level of radiopacity for a given amount of material is expected. These types of processes are, however, costly and of limited use in the mass production of plastic medical devices.

SUMMARY OF THE INVENTION

The present invention relates to a flexible plastic laminate composition with radiopaque properties. The laminate composition includes a single or multiple layers of a plastic material and a single or multiple layers of radiopaque or conductive materials wherein the radiopaque or conductive material forms a discrete and separate layer applied via a solvent between the layers of a plastic material. The use of a solvent allows the radiopaque material to be adhered to a surface of the plastic material upon evaporation of the solvent. This results in the formation of a uniform and thin layer of radiopaque material within the laminate composition such that desired radiopaque properties can be achieved.

The laminate composition can be formed into various geometries, such as tubular parts that can be cut to desired lengths to form compliant radiopaque marker bands. The radiopaque marker bands are flexible and made, in part, from a plastic material. This allows the marker bands to be readily applied to medical devices, such as catheters, for radiographic imaging. Alternatively, the laminate compositions can be utilized to form the catheter or other suitable medical device.

In an embodiment, the present invention provides a flexible laminate composition that includes one or more discrete and separate layers of a radiopaque material. The composition includes one or more plastic layers composed of a plastic material and one or more radiopaque layers composed of a radiopaque material wherein at least one of the radiopaque layers is applied via a solvent to at least one of the plastic layers.

In another embodiment, the present invention provides a method of manufacturing a flexible laminate composition. The method includes forming a radiopaque solution including a radiopaque material; and applying the radiopaque material via a solvent to a plastic layer composed of a plastic material; and forming a uniform layer of the radiopaque material on the plastic material. As a result, a uniform and thin layer of the radiopaque material can be readily formed such that a desired level of radiopaque properties associated with the laminate can be achieved.

Additional features and advantages of the present invention are described in, and will be apparent from, the following Detailed Description of the Invention and the figures.

DETAILED DESCRIPTION OF THE INVENTION

Figure 1:
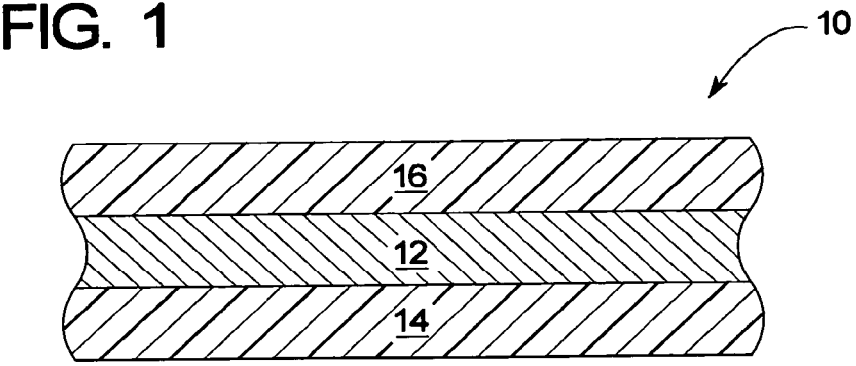
FIG. 1 illustrates a laminate composition pursuant to an embodiment of the present invention.

The present invention relates to laminate compositions. More specifically, the present invention relates to flexible and plastic laminate compositions that include a discrete and separate layer of a radiopaque material.

The laminate composition of the present invention includes a single or multiple layers of a plastic material and a single or multiple layers of radiopaque or conductive materials wherein the radiopaque or conductive material forms a discrete and separate layer applied via a solvent between the layers of plastic material. As a result, the laminate composition includes a uniform and thin layer of radiopaque material such that a desired and suitable level of radiopaque qualities can be achieved.

The laminate composition can be formed into various geometries, such as tubular parts that can be cut to desired lengths to form compliant radiopaque marker bands. The radiopaque marker bands are flexible and made, in part, from a plastic material. This allows the marker bands to be readily applied to medical devices, such as catheters, for radiographic imaging. Alternatively, the laminate compositions can be utilized to form the catheter or other suitable medical device.

The laminate composition can include any suitable type and amount of materials. As previously discussed, the laminate composition includes layers of radiopaque and plastic materials wherein the radiopaque material layers are applied via a solvent to the plastic material layers. The radiopaque material includes bismuth oxychloride, bismuth subcarbonate, bismuth trioxide, barium sulfate, tungsten, tantlium, platinum, silver, gold, copper, carbon, the like and combinations thereof.

The radiopaque material can include any suitable particle size such that it can be applied to the plastic material by adhering thereto with the use of a solvent, such as methyl ethyl ketone, tetrahydroform, dimethyl formamide, toluene, acetone, heptane, cyclohexane, the like and combinations thereof. Preferably, the radiopaque material has a particle size that ranges from about 2 microns to about 120 mesh screen size. In an embodiment, the radiopaque material is a perforated metal foil.

The plastic material can include any suitable type and amount of plastic material. In an embodiment, the plastic material includes a solution grade plastic coating resin, such as polyurethane, polyester, polyether, polycaprolactone, a copolymer of vinyl chloride and vinyl acetate, polyvinyl chloride, a silicone elastomer, the like and combinations thereof.

The plastic material can be made in any suitable manner. For example, the plastic material can be made from a solution grade plastic in a solvent that allows for the formation of different shapes. This can be conducted with the use of mandrels, forms or the like that are coated with the plastic solution. The solvent for the solution grade plastic can include, for example, methyl ethyl ketone, tetrahydrofuran, dimethylformamide, toluene, acetone, heptane, cyclohexane, the like, and combinations thereof.

As the solvent evaporates, the plastic is reconstituted on the form. When the form is removed, the plastic retains it shape and has the strength of the original material. The form can include any suitable type of shapes and sizes, such as a tubular part with a lubricous surface.

The radiopaque material is adhered through the application of an additional solvent or solvents to the surface of the formed plastic. The solvent or solvents create a tacky surface and thus cause the surface to flow and allow the adhesion and encapsulation of the radiopaque material. Once the solvent evaporates, the radiopaque material is retained on the surface of the plastic material thereby forming a uniform and thin layer of the radiopaque material.

Multiple applications of the plastic coating, solvent and radiopaque material result in a laminated plastic structure where the radiopaque material is not dispersed into the plastic. Instead, the radiopaque material is deposited as a uniform and thin layer lamination. The uniform thin layer of radiopaque material can enhance the ability of the laminate composition to block x-ray radiation as compared to conventional radiopaque materials, such as an aggregate of dispersed radiopaque materials in a molded or an extruded part. The use of the solvent allows the uniform thin layer of radiopaque material to be formed within the laminate composition with relative ease in operation, thus facilitating the manufacture of the radiopaque laminate in mass production.

Figure 2:
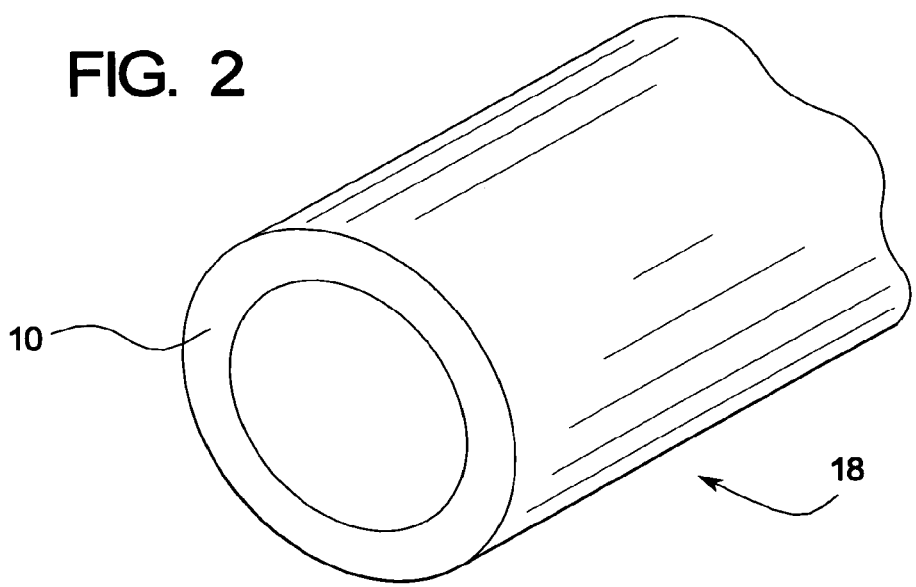
FIG. 2 illustrates a radiopaque marker band pursuant to an embodiment of the present invention.
Figure 3:
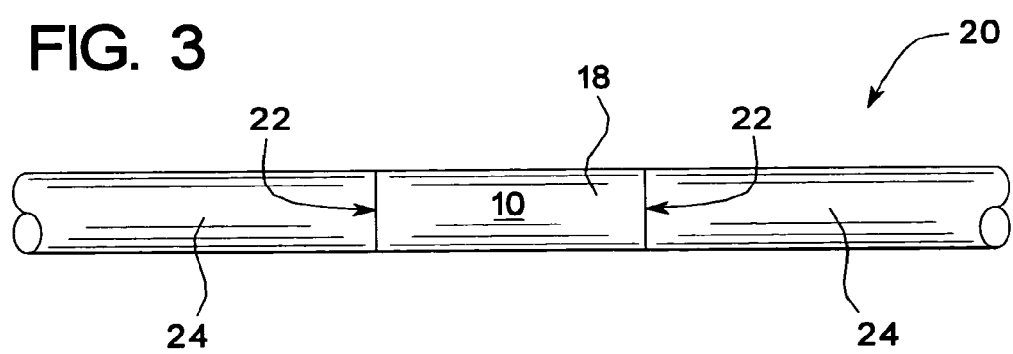
FIG. 3 illustrates a catheter with a radiopaque marker band pursuant to an embodiment of the present invention.

FIGS. 1-3 provide graphical representations that illustrate various embodiments of the present invention. FIG. 1 illustrates a sectional view of a laminate composition 10 according to an embodiment. As shown, a radiopaque material 12 is applied between a first plastic layer 14 and a second plastic layer 16. As previously discussed, the radiopaque material is applied to the plastic layers with the use of a solvent. The solvent produces a tacky surface such that the radiopaque material can effectively adhere upon evaporation of the solvent. This results in a uniform thin layer of radiopaque material within the laminate composition. The laminate composition can include multiple layers of plastic material and radiopaque material depending on the type of application.

As previously discussed, the laminate compositions of the present invention can be formed into any suitable types of configurations. As shown in FIG. 2, the laminate composition 10 is formed into a radiopaque marker band 18. The marker band 18 can be applied to a catheter 20 via RF bonding 22, heat bonding, or other suitable technique to a part 24 of the catheter 20 as shown in FIG. 3. Alternatively, the laminate composition can be formed into the catheter or other suitable type of medical device in any suitable manner.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method of manufacturing a flexible laminate composition, the method comprising:
   applying a particulate radiopaque material via a solvent directly to a plastic layer composed of a plastic material, such that the solvent allows encapsulation of the particulate material by the plastic layer to form a uniform layer of the radiopaque material.

2. The method of claim 1, wherein the solvent is selected from the group consisting of methyl ethyl ketone, tetrahydrofuran, dimethylformamide, toluene, acetone, heptane, cyclohexane, and combinations thereof.

3. The method of claim 1, wherein the radiopaque material has a particle size that ranges from about 2 microns to about 120 mesh screen size.

4. The method of claim 1, wherein the radiopaque material comprises particles obtained from perforating metal foil.

5. The method of claim 1, wherein the flexible laminate composition is formed into a medical device including a catheter.

6. The method of claim 1, wherein the flexible laminate composition is formed into a radiopaque marker band that can be applied to a medical device.

7. The method of claim 1, wherein the radiopaque material is selected from the group consisting of bismuth oxychloride, bismuth subcarbonate, bismuth trioxide, barium sulfate, tungsten, tantalum, platinum, silver, gold, copper, carbon and mixtures thereof.

8. The method of claim 1, wherein the plastic material includes a solution grade plastic coating resin selected from the group consisting of polyurethane, polyester, polyether, polycaprolactone, vinyl chloride, vinyl acetate, polyvinyl chloride, silicone elastomer, and combinations thereof.

* * * * *